United States Patent
LeMay et al.

(10) Patent No.: US 9,737,443 B2
(45) Date of Patent: Aug. 22, 2017

(54) ERGONOMIC TAMPON APPLICATOR

(71) Applicant: Edgewell Personal Care Brands, LLC, Chesterfield, MO (US)

(72) Inventors: Jessica LeMay, Paramus, NJ (US); Kathryn Bennett, Fairfield, CT (US); Keith Edgett, Ramsey, NJ (US); Dane Jackson, Bloomingdale, NJ (US); Mario Turchi, Tenafly, NJ (US); Susanne Weber, New York, NY (US)

(73) Assignee: Edgewell Personal Care Brands, LLC, Chesterfield, MO (US)

( * ) Notice: Subject to any disclaimer, the term of this patent is extended or adjusted under 35 U.S.C. 154(b) by 13 days.

(21) Appl. No.: 14/576,473

(22) Filed: Dec. 19, 2014

(65) Prior Publication Data

US 2015/0105711 A1    Apr. 16, 2015

Related U.S. Application Data

(63) Continuation of application No. 13/669,840, filed on Nov. 6, 2012, now Pat. No. 9,421,135, which is a
(Continued)

(51) Int. Cl.
| | |
|---|---|
| *A61F 13/20* | (2006.01) |
| *A61F 13/26* | (2006.01) |
| *A61F 13/34* | (2006.01) |

(52) U.S. Cl.
CPC ............ *A61F 13/266* (2013.01); *A61F 13/26* (2013.01); *A61F 13/2077* (2013.01);
(Continued)

(58) Field of Classification Search
CPC ...... A61F 13/26; A61F 13/263; A61F 13/266; A61F 13/34; A61F 13/2077
(Continued)

(56) References Cited

U.S. PATENT DOCUMENTS

| | | | |
|---|---|---|---|
| 1,191,736 A | 7/1916 | Roberson |
| 1,218,478 A | 3/1917 | Sappington |
| 1,554,690 A | 9/1925 | Pride |
| 1,555,708 A | 9/1925 | Gale |
| 1,731,665 A | 10/1929 | Huebsch |
| 2,077,231 A | 4/1937 | Fourness et al. |

(Continued)

FOREIGN PATENT DOCUMENTS

| | | |
|---|---|---|
| AU | 8774659 | 1/1988 |
| BE | 667613 | 1/1966 |

(Continued)

OTHER PUBLICATIONS

Decision of Rejection dated Dec. 4. 2013 from corresponding Japanese Application No. 2009-552722.
(Continued)

*Primary Examiner* — Jacqueline Stephens
(74) *Attorney, Agent, or Firm* — Edgewell Personal Care Brands, LLC

(57) ABSTRACT

A tampon applicator barrel includes an insertion tip at a forward end of the barrel, a main body section that extends from the insertion tip, and a reverse taper section that is joined to the main body section so that the main body section is between the insertion tip and the reverse taper section. The main body section tapers toward the insertion tip section. The reverse taper section tapers in a direction away from the insertion tip section. A finger grip section extends from the reverse taper section to a plunger receiving end of the barrel opposite the forward end. The barrel is straight from the forward end to the plunger receiving end that receives a plunger.

76 Claims, 2 Drawing Sheets

Related U.S. Application Data continuation of application No. 12/798,990, filed on Apr. 15, 2010, now Pat. No. 8,337,478, which is a continuation of application No. 10/242,474, filed on Sep. 12, 2002, now Pat. No. 7,727,208.

(52) U.S. Cl.
CPC ............ *A61F 13/263* (2013.01); *A61F 13/34* (2013.01); *Y10S 604/904* (2013.01)

(58) Field of Classification Search
USPC .............. 604/904, 385.17, 385.18, 285, 286, 604/11–18, 311
See application file for complete search history.

(56) References Cited

U.S. PATENT DOCUMENTS

| | | |
|---|---|---|
| 2,095,377 A | 10/1937 | Breese |
| 2,099,931 A | 11/1937 | Fourness |
| 2,123,750 A | 7/1938 | Schulz |
| 2,178,704 A | 11/1939 | Robinson |
| 2,222,088 A | 11/1940 | Petersen |
| 2,254,272 A | 9/1941 | Crockford |
| 2,301,868 A | 11/1942 | Gurley, Jr. et al. |
| 2,306,406 A | 12/1942 | Robinson |
| 2,330,257 A | 9/1943 | Bailey |
| 2,386,590 A | 10/1945 | Calhoun |
| 2,413,480 A | 12/1946 | Winter |
| 2,458,685 A | 1/1949 | Crockford |
| 2,476,956 A | 7/1949 | Bonham |
| 2,489,502 A | 11/1949 | Ruth |
| 2,409,414 A | 3/1950 | Rabell |
| 2,499,444 A | 3/1950 | Allison |
| 2,607,346 A | 8/1952 | Milcent |
| 2,706,986 A | 4/1955 | Carrier |
| 2,761,449 A | 9/1956 | Bletzinger |
| 2,799,055 A | 7/1957 | Carrier |
| 2,854,978 A | 10/1958 | Millman et al. |
| 2,877,767 A | 3/1959 | Schwartz |
| 3,204,635 A | 9/1965 | Voss et al. |
| 3,264,691 A | 8/1966 | Whitehead |
| 3,291,130 A | 12/1966 | Whitehead |
| 3,306,294 A | 2/1967 | Penska |
| 3,306,295 A | 2/1967 | Penska |
| 3,347,234 A | 10/1967 | Voss |
| 3,358,354 A | 12/1967 | Voss et al. |
| 3,369,544 A | 2/1968 | Crockford |
| 3,397,695 A | 8/1968 | Voss |
| 3,431,909 A | 3/1969 | Krusko |
| 3,431,910 A | 3/1969 | Kokx |
| 3,433,225 A | 3/1969 | Voss et al. |
| 3,520,302 A | 7/1970 | Jones |
| 3,570,489 A | 3/1971 | Brown |
| 3,572,341 A | 3/1971 | Glassman |
| 3,575,169 A | 4/1971 | Voss et al. |
| 3,595,236 A | 7/1971 | Corrigan |
| 3,606,643 A | 9/1971 | Mooney |
| 3,628,533 A | 12/1971 | Loyer |
| 3,643,661 A | 2/1972 | Crockford |
| 3,683,915 A | 8/1972 | Voss |
| 3,690,321 A | 9/1972 | Hirschman |
| 3,695,270 A | 10/1972 | Dostal |
| 3,699,965 A | 10/1972 | Dostal |
| 3,706,311 A | 12/1972 | Kokx et al. |
| 3,710,793 A | 1/1973 | Glassman |
| 3,712,305 A | 1/1973 | Wennerblom et al. |
| 3,726,277 A | 4/1973 | Hirschman |
| 3,731,687 A | 5/1973 | Glassman |
| 3,738,364 A | 6/1973 | Brien et al. |
| 3,762,413 A | 10/1973 | Hanke |
| 3,765,416 A | 10/1973 | Werner et al. |
| 3,794,029 A | 2/1974 | Dulle |
| 3,811,445 A | 5/1974 | Dostal |
| 3,812,856 A | 5/1974 | Duncan et al. |
| 3,834,389 A | 9/1974 | Dulle |
| 3,845,767 A | 11/1974 | Friese et al. |
| 3,856,013 A | 12/1974 | Dulle |
| 3,858,571 A | 1/1975 | Rudolph |
| 3,885,563 A | 5/1975 | Johnson et al. |
| 3,905,372 A | 9/1975 | Denkinger |
| 3,946,737 A | 3/1976 | Kobler |
| 3,954,104 A | 5/1976 | Kraskin et al. |
| 3,971,378 A | 7/1976 | Krantz |
| 3,981,305 A | 9/1976 | Ring |
| 3,983,873 A | 10/1976 | Hirschman |
| 3,994,298 A | 11/1976 | Des Marais |
| 4,010,751 A | 3/1977 | Ring |
| 4,018,255 A | 4/1977 | Diggs |
| 4,027,673 A | 6/1977 | Poncy et al. |
| 4,048,998 A | 9/1977 | Nigro |
| 4,077,408 A | 3/1978 | Murray et al. |
| 4,077,409 A | 3/1978 | Murray et al. |
| 4,099,976 A | 7/1978 | Kraskin et al. |
| 4,108,180 A | 8/1978 | Moehrle |
| D250,663 S | 12/1978 | Koch et al. |
| 4,175,457 A | 11/1979 | Lashley |
| 4,185,631 A | 1/1980 | McConnell |
| 4,186,742 A | 2/1980 | Donald |
| 4,198,978 A | 4/1980 | Nigro |
| 4,211,225 A | 7/1980 | Sibalis |
| 4,212,301 A | 7/1980 | Johnson |
| 4,217,900 A | 8/1980 | Wiegner et al. |
| 4,266,546 A | 5/1981 | Roland et al. |
| 4,271,835 A | 6/1981 | Conn et al. |
| 4,274,412 A | 6/1981 | Austin |
| 4,278,088 A | 7/1981 | Reeves et al. |
| 4,291,696 A | 9/1981 | Ring |
| 4,294,253 A | 10/1981 | Friese |
| 4,308,867 A | 1/1982 | Roseman et al. |
| 4,309,997 A | 1/1982 | Donald |
| 4,312,348 A | 1/1982 | Friese |
| 4,318,407 A | 3/1982 | Woon |
| 4,328,804 A | 5/1982 | Shimatani |
| 4,335,720 A | 6/1982 | Glassman |
| 4,335,721 A | 6/1982 | Matthews |
| 4,341,211 A | 7/1982 | Kline |
| 4,341,214 A | 7/1982 | Fries et al. |
| 4,351,339 A | 9/1982 | Sneider |
| 4,361,150 A | 11/1982 | Voss |
| 4,361,151 A | 11/1982 | Fitzgerald |
| 4,373,529 A | 2/1983 | Lilaonitkul et al. |
| 4,421,504 A | 12/1983 | Kline |
| 4,424,054 A | 1/1984 | Conn et al. |
| 4,428,370 A | 1/1984 | Keely |
| 4,475,911 A | 10/1984 | Gellert |
| D279,504 S | 7/1985 | Tump |
| 4,536,178 A | 8/1985 | Lichstein et al. |
| 4,543,086 A | 9/1985 | Johnson |
| 4,543,098 A | 9/1985 | Wolfe et al. |
| 4,553,965 A | 11/1985 | Conn et al. |
| D287,876 S | 1/1987 | Blatherwick et al. |
| 4,676,773 A | 6/1987 | Sheldon |
| 4,726,805 A | 2/1988 | Sanders, III |
| 4,743,237 A | 5/1988 | Sweere |
| 4,755,166 A | 7/1988 | Olmstead |
| 4,787,895 A | 11/1988 | Stokes et al. |
| 4,845,922 A | 7/1989 | Sweere |
| 4,846,802 A | 7/1989 | Sanders, III |
| 4,881,644 A | 11/1989 | Norquest et al. |
| 4,891,042 A | 1/1990 | Melvin et al. |
| 4,973,302 A | 11/1990 | Armour et al. |
| 5,004,467 A | 4/1991 | Hinzmann et al. |
| 5,019,061 A | 5/1991 | Hoden et al. |
| 5,047,024 A | 9/1991 | Glassman |
| 5,084,038 A | 1/1992 | Sheldon et al. |
| 5,112,348 A | 5/1992 | Glassman |
| 5,133,457 A | 7/1992 | Kadel |
| 5,149,332 A | 9/1992 | Walton et al. |
| 5,153,971 A | 10/1992 | Van Iten |
| 5,158,535 A | 10/1992 | Paul et al. |
| 5,213,566 A | 5/1993 | Weissenburger |
| 5,267,953 A | 12/1993 | Paul et al. |
| 5,279,541 A | 1/1994 | Frayman et al. |

(56) References Cited

U.S. PATENT DOCUMENTS

| | | |
|---|---|---|
| 5,290,501 A | 3/1994 | Klesius |
| 5,342,331 A | 8/1994 | Silber et al. |
| 5,350,371 A | 9/1994 | Van Iten |
| 5,364,383 A | 11/1994 | Hayes et al. |
| 5,370,633 A | 12/1994 | Villalta |
| 5,387,206 A | 2/1995 | Valentine et al. |
| 5,389,067 A | 2/1995 | Rejai |
| 5,395,308 A | 3/1995 | Fox et al. |
| 5,403,300 A | 4/1995 | Howarth |
| 5,417,224 A | 5/1995 | Petrus et al. |
| 5,437,628 A | 8/1995 | Fox et al. |
| 5,443,776 A | 8/1995 | Bartholomew et al. |
| 5,445,605 A | 8/1995 | Pluss |
| 5,542,914 A | 8/1996 | Van Iten |
| 5,547,701 A | 8/1996 | Nielsen et al. |
| 5,554,108 A | 9/1996 | Browning et al. |
| 5,584,827 A | 12/1996 | Korteweg et al. |
| 5,592,725 A | 1/1997 | Brinker |
| 5,634,248 A | 6/1997 | McNelis et al. |
| 5,659,934 A | 8/1997 | Jessup et al. |
| 5,681,894 A | 10/1997 | Williams et al. |
| 5,683,358 A | 11/1997 | Nielsen et al. |
| 5,693,009 A | 12/1997 | Fox et al. |
| 5,718,675 A | 2/1998 | Leijd |
| 5,738,646 A | 4/1998 | Fox et al. |
| 5,755,906 A | 5/1998 | Achter et al. |
| 5,766,145 A | 6/1998 | Fox et al. |
| 5,772,645 A | 6/1998 | Zadini et al. |
| 5,782,794 A | 7/1998 | Assenheimer et al. |
| 5,788,910 A | 8/1998 | McNelis et al. |
| 5,792,096 A | 8/1998 | Rentmeester et al. |
| 5,795,346 A | 8/1998 | Achter et al. |
| 5,800,338 A | 9/1998 | Kollerup et al. |
| 5,804,653 A | 9/1998 | Weng |
| 5,807,372 A | 9/1998 | Balzar |
| 5,817,047 A | 10/1998 | Osborn, III et al. |
| 5,827,251 A | 10/1998 | Moder et al. |
| 5,873,971 A | 2/1999 | Balzar |
| 5,891,081 A | 4/1999 | McNelis et al. |
| 5,891,123 A | 4/1999 | Balzar |
| 5,891,127 A | 4/1999 | Moder et al. |
| 5,911,712 A | 6/1999 | Leutwyler et al. |
| 5,928,183 A | 7/1999 | Fox et al. |
| 5,928,184 A | 7/1999 | Etheredge et al. |
| 5,931,903 A | 9/1999 | Jackson |
| 5,947,992 A | 9/1999 | Zadini et al. |
| 5,954,683 A | 9/1999 | Downs et al. |
| 5,964,741 A | 10/1999 | Moder et al. |
| 5,986,000 A | 11/1999 | Williams et al. |
| 5,986,165 A | 11/1999 | Moder et al. |
| 6,003,216 A | 12/1999 | Hull, Jr. et al. |
| 6,019,743 A | 2/2000 | Cole et al. |
| 6,039,716 A | 3/2000 | Jessup et al. |
| 6,039,828 A | 3/2000 | Achter et al. |
| 6,045,526 A | 4/2000 | Jackson |
| 6,068,899 A | 5/2000 | Osborn, III et al. |
| 6,071,259 A | 6/2000 | Steiger et al. |
| 6,090,038 A | 7/2000 | Zunker et al. |
| 6,095,998 A | 8/2000 | Osborn et al. |
| 6,095,999 A | 8/2000 | Jackson et al. |
| 6,142,928 A | 11/2000 | Zunker et al. |
| 6,177,606 B1 | 1/2001 | Etheredge et al. |
| 6,177,608 B1 | 1/2001 | Weinstrauch |
| 6,179,802 B1 | 1/2001 | Jackson |
| 6,180,051 B1 | 1/2001 | Schoelling |
| 6,183,436 B1 | 2/2001 | Korteweg et al. |
| 6,186,994 B1 | 2/2001 | Bowles et al. |
| 6,190,348 B1 | 2/2001 | Tiemann et al. |
| 6,191,341 B1 | 2/2001 | Shippert |
| 6,196,988 B1 | 3/2001 | Cole et al. |
| 6,203,515 B1 | 3/2001 | Norquest et al. |
| 6,206,867 B1 | 3/2001 | Osborn et al. |
| 6,248,274 B1 | 6/2001 | Williams |
| 6,254,565 B1 | 7/2001 | Williams et al. |
| 6,254,566 B1 | 7/2001 | Buck et al. |
| 6,264,626 B1 | 7/2001 | Linares et al. |
| 6,270,470 B1 | 8/2001 | Buck et al. |
| 6,283,952 B1 | 9/2001 | Child et al. |
| 6,299,573 B1 | 10/2001 | Hull, Jr. et al. |
| 6,302,861 B2 | 10/2001 | Tweddell, III et al. |
| 6,302,862 B1 | 10/2001 | Osborn, III et al. |
| 6,310,269 B1 | 10/2001 | Friese et al. |
| 6,358,235 B1 | 3/2002 | Osborn, III et al. |
| 6,368,442 B1 | 4/2002 | Linares et al. |
| 6,380,455 B1 | 4/2002 | Moder et al. |
| 6,416,488 B1 | 7/2002 | Jackson et al. |
| 6,419,777 B1 | 7/2002 | Achter et al. |
| 6,423,025 B1 | 7/2002 | Buzot |
| 6,432,075 B1 | 8/2002 | Wada et al. |
| 6,432,076 B1 | 8/2002 | Wada et al. |
| 6,432,246 B1 | 8/2002 | Blake |
| 6,450,986 B1 | 9/2002 | Binner et al. |
| 6,465,713 B1 | 10/2002 | Gell et al. |
| 6,478,764 B1 | 11/2002 | Suga |
| D467,599 S | 12/2002 | Brazell |
| 6,500,140 B1 | 12/2002 | Cole et al. |
| 6,506,958 B2 | 1/2003 | Williams |
| 6,508,780 B1 | 1/2003 | Edgett et al. |
| 6,511,452 B1 | 1/2003 | Rejai et al. |
| 6,545,283 B1 | 4/2003 | Williams et al. |
| 6,570,052 B2 | 5/2003 | Zadini et al. |
| 6,572,577 B1 | 6/2003 | Binner et al. |
| D477,075 S | 7/2003 | Schoelling |
| 6,585,300 B1 | 7/2003 | Rajala et al. |
| 6,595,974 B1 | 7/2003 | Pauley et al. |
| 6,603,054 B2 | 8/2003 | Chen et al. |
| 6,610,025 B2 | 8/2003 | Berg et al. |
| 6,635,205 B2 | 10/2003 | Williams et al. |
| 6,645,136 B1 | 11/2003 | Zunker et al. |
| 6,648,846 B2 | 11/2003 | Binner et al. |
| 6,654,992 B2 | 12/2003 | Rajala et al. |
| 6,685,787 B2 | 2/2004 | Linares et al. |
| 6,685,788 B2 | 2/2004 | Linares et al. |
| 6,719,743 B1 | 4/2004 | Wada |
| 6,730,057 B2 | 5/2004 | Zhao et al. |
| 6,740,070 B2 | 5/2004 | Agyapong et al. |
| D492,033 S | 6/2004 | Jarmon et al. |
| 6,746,418 B1 | 6/2004 | Pauley et al. |
| 6,756,434 B1 | 6/2004 | Williams et al. |
| 6,773,423 B2 | 8/2004 | Osborn et al. |
| 6,814,722 B2 | 11/2004 | Jackson et al. |
| 6,830,554 B2 | 12/2004 | Jackson et al. |
| 6,887,226 B2 | 5/2005 | Cassoni et al. |
| 6,932,805 B2 | 8/2005 | Domeier et al. |
| 6,958,057 B2 | 10/2005 | Berg et al. |
| D511,832 S | 11/2005 | Bellofatto et al. |
| D515,212 S | 2/2006 | Edgett et al. |
| 7,044,928 B2 | 5/2006 | LeMay et al. |
| 7,081,110 B2 | 7/2006 | Karapasha |
| 7,098,292 B2 | 8/2006 | Zhao et al. |
| 7,160,279 B2 | 1/2007 | Pauley et al. |
| 7,172,573 B1 | 2/2007 | Lamb et al. |
| 7,226,436 B2 | 6/2007 | Gorham et al. |
| 7,250,129 B2 | 7/2007 | Williams et al. |
| 7,259,129 B2 | 8/2007 | Matusz et al. |
| 7,335,194 B2 | 2/2008 | Wada |
| 7,387,622 B1 | 6/2008 | Pauley et al. |
| D572,362 S | 7/2008 | Edgett et al. |
| D579,113 S | 10/2008 | Edgett et al. |
| D612,940 S | 3/2010 | Edgett et al. |
| 7,704,242 B2 | 4/2010 | LeMay et al. |
| D626,650 S | 11/2010 | Edgett et al. |
| D639,864 S | 6/2011 | Woelfel |
| D652,848 S | 1/2012 | Flanagan et al. |
| 8,198,504 B2 | 6/2012 | Glaug et al. |
| 8,372,027 B2 | 2/2013 | LeMay et al. |
| 8,444,590 B2 | 5/2013 | LeMay et al. |
| 8,571,883 B2 | 10/2013 | Dougherty et al. |
| 8,696,957 B2 | 4/2014 | Dougherty et al. |
| 9,107,775 B2 | 8/2015 | Edgett et al. |
| 2002/0010413 A1 | 1/2002 | Binner et al. |
| 2002/0010447 A1 | 1/2002 | Williams et al. |
| 2002/0038109 A1 | 3/2002 | Williams |
| 2002/0107497 A1 | 8/2002 | Osborn et al. |

(56) References Cited

U.S. PATENT DOCUMENTS

| | | |
|---|---|---|
| 2002/0133135 A1 | 9/2002 | Gell et al. |
| 2002/0143287 A1 | 10/2002 | Buzot |
| 2002/0143303 A1 | 10/2002 | Intravartolo et al. |
| 2002/0147436 A1 | 10/2002 | Gell et al. |
| 2002/0151859 A1 | 10/2002 | Schoelling |
| 2002/0156442 A1 | 10/2002 | Jackson et al. |
| 2002/0177835 A1 | 11/2002 | Zadini et al. |
| 2002/0183681 A1 | 12/2002 | Bernard |
| 2002/0188264 A1 | 12/2002 | Knuth et al. |
| 2002/0188283 A1 | 12/2002 | Binner et al. |
| 2003/0028176 A1 | 2/2003 | Berg et al. |
| 2003/0028177 A1 | 2/2003 | Berg et al. |
| 2003/0036721 A1 | 2/2003 | Zhao et al. |
| 2003/0040695 A1 | 2/2003 | Zhao et al. |
| 2003/0055391 A1 | 3/2003 | Nguyen et al. |
| 2003/0073948 A1 | 4/2003 | Binner et al. |
| 2003/0100871 A1 | 5/2003 | Mauro et al. |
| 2003/0105421 A1 | 6/2003 | Jarmon et al. |
| 2003/0125658 A1 | 7/2003 | Marvin |
| 2003/0135180 A1 | 7/2003 | Nguyen et al. |
| 2003/0149416 A1 | 8/2003 | Cole et al. |
| 2003/0158533 A1 | 8/2003 | Agyapong et al. |
| 2003/0163080 A1 | 8/2003 | LeMay et al. |
| 2003/0167048 A1 | 9/2003 | Policappelli |
| 2003/0172504 A1 | 9/2003 | Sageser et al. |
| 2003/0176844 A1 | 9/2003 | Randall et al. |
| 2003/0176845 A1 | 9/2003 | Kollwitz et al. |
| 2003/0208179 A1 | 11/2003 | Fuchs et al. |
| 2003/0208180 A1 | 11/2003 | Fuchs et al. |
| 2003/0216680 A1 | 11/2003 | Binner et al. |
| 2003/0236485 A1 | 12/2003 | Fedyk et al. |
| 2004/0000222 A1 | 1/2004 | Rejai |
| 2004/0010220 A1 | 1/2004 | Miller et al. |
| 2004/0054317 A1 | 3/2004 | LeMay et al. |
| 2004/0064082 A1 | 4/2004 | LeMay et al. |
| 2004/0153024 A1 | 8/2004 | Pauley et al. |
| 2004/0193131 A1 | 9/2004 | Wada |
| 2004/0199100 A1 | 10/2004 | LeMay et al. |
| 2004/0199101 A1 | 10/2004 | LeMay et al. |
| 2004/0199102 A1 | 10/2004 | LeMay et al. |
| 2004/0225269 A1 | 11/2004 | Zhao et al. |
| 2004/0243088 A1 | 12/2004 | LeMay et al. |
| 2005/0015041 A1 | 1/2005 | Karapasha |
| 2005/0020964 A1 | 1/2005 | Melvin et al. |
| 2005/0022349 A1 | 2/2005 | Pham et al. |
| 2005/0070839 A1 | 3/2005 | Jackson et al. |
| 2005/0080393 A1 | 4/2005 | Policappelli |
| 2005/0096617 A1 | 5/2005 | Gorham et al. |
| 2005/0096619 A1 | 5/2005 | Costa |
| 2005/0177091 A1 | 8/2005 | Jarmon et al. |
| 2007/0026228 A1 | 2/2007 | Hartmann et al. |
| 2007/0156081 A1 | 7/2007 | Karapasha |
| 2007/0232982 A1 | 10/2007 | Jarmon et al. |
| 2007/0260211 A1 | 11/2007 | Schmidt-Forst |
| 2007/0276317 A1 | 11/2007 | Henderson et al. |
| 2007/0293809 A1 | 12/2007 | Karapasha |
| 2008/0033337 A1 | 2/2008 | Dougherty et al. |
| 2008/0058751 A1 | 3/2008 | Edgett et al. |
| 2008/0119778 A1 | 5/2008 | Jorgensen et al. |
| 2008/0132868 A1 | 6/2008 | Jorgensen et al. |
| 2008/0167597 A1 | 7/2008 | Dougherty |
| 2008/0221502 A1 | 9/2008 | Binner et al. |
| 2008/0287902 A1 | 11/2008 | Edgett et al. |
| 2009/0036859 A1 | 2/2009 | Dougherty et al. |
| 2009/0156979 A1 | 6/2009 | Andersch |
| 2009/0227975 A1 | 9/2009 | Dougherty et al. |
| 2009/0234268 A1 | 9/2009 | Jorgensen et al. |
| 2009/0247981 A1 | 10/2009 | Glaug et al. |
| 2009/0281474 A1 | 11/2009 | Dougherty et al. |
| 2009/0281514 A1 | 11/2009 | Dougherty et al. |
| 2010/0036309 A1 | 2/2010 | Jorgensen et al. |
| 2010/0120707 A1 | 5/2010 | Dougherty et al. |
| 2010/0198133 A1 | 8/2010 | Dougherty et al. |
| 2012/0061867 A1 | 3/2012 | Dougherty et al. |

FOREIGN PATENT DOCUMENTS

| | | |
|---|---|---|
| BE | 758152 | 4/1971 |
| CA | 11086099 | 9/1980 |
| CA | 1110401 | 10/1981 |
| CA | 2024473 | 3/1991 |
| CA | 2095390 | 11/1993 |
| CA | 2143083 | 2/1996 |
| CA | 2145692 | 2/1996 |
| CA | 2153818 | 2/1996 |
| CA | 2280251 | 2/2000 |
| CA | 2302065 | 9/2000 |
| CA | 2325269 | 5/2001 |
| CA | 2325669 | 5/2001 |
| CA | 108982 S | 8/2006 |
| CA | 115880 S | 8/2008 |
| CA | 2441647 C | 5/2009 |
| DE | 1920773 | 12/1969 |
| DE | 3328910 | 2/1985 |
| DE | 3540725 | 5/1986 |
| DE | 3726311 | 2/1989 |
| DE | 4446226 | 6/1995 |
| DE | 19726648 | 12/1998 |
| EP | 110793 | 12/1983 |
| EP | 158543 | 3/1985 |
| EP | 0243250 | 10/1987 |
| EP | 546256 | 7/1992 |
| EP | 797971 | 10/1997 |
| FR | 1515087 | 3/1968 |
| FR | 2567399 | 7/1984 |
| GB | 2097259 | 11/1982 |
| GB | 8428462 A | 12/1984 |
| GB | 9419135 | 11/1994 |
| GB | 2414394 B | 1/2006 |
| GB | 2415626 B | 3/2006 |
| IL | 154877 | 7/2009 |
| IL | 163734 | 12/2009 |
| JP | H05-68695 | 3/1993 |
| JP | 10024064 | 1/1998 |
| JP | 2000288018 | 10/2000 |
| JP | 2001-008964 | 1/2001 |
| JP | 200117465 | 1/2001 |
| JP | 2001145658 | 5/2001 |
| JP | 2005-526584 | 9/2005 |
| JP | HO62-027952 | 9/2005 |
| JP | 2005531345 | 10/2005 |
| WO | 8000008 | 1/1980 |
| WO | 93/08779 | 5/1993 |
| WO | 94/15564 | 7/1994 |
| WO | 9605795 | 2/1996 |
| WO | 9637173 | 11/1996 |
| WO | 9640032 | 12/1996 |
| WO | 9806366 | 2/1998 |
| WO | 9900097 | 1/1999 |
| WO | 0037013 | 6/2000 |
| WO | 0066213 | 11/2000 |
| WO | 0197735 | 12/2001 |
| WO | 0200153 | 1/2002 |
| WO | 0202176 | 1/2002 |
| WO | 0226159 | 4/2002 |
| WO | 02074352 | 9/2002 |
| WO | 03032883 | 4/2003 |
| WO | 03101362 A2 | 11/2003 |
| WO | 2004000160 | 12/2003 |
| WO | 2004/098449 | 11/2004 |
| WO | 2005112856 A1 | 12/2005 |
| WO | 2005112862 A1 | 12/2005 |
| WO | 2006016933 A1 | 2/2006 |
| WO | 2006037157 | 4/2006 |
| ZA | 9305011 | 2/1994 |

OTHER PUBLICATIONS

Official Action dated Jan. 22. 2012 from corresponding Mexican Application No. MX/a/2009/009468.
Decision of Rejection dated Dec. 11. 2012 from corresponding Japanese Application No. 2009-552722.

(56) References Cited

OTHER PUBLICATIONS

Official Action dated Jan. 22. 2013 from corresponding Mexican Application No. MX/a/2009/009468.
Official Notice of Final Rejection dated Feb. 27, 2012 From Korean Application No. 10-2009-7020746.
Notice of Notice of Reasons for Rejection dated Feb. 20, 2012 from Japanese Application No. 2009-552722.Reasons for Rejection dated Feb. 20, 2012 from Japanese Application No. 2009-552722.
Canadian Office Action dated Apr. 6, 2011 for corresponding Canadian Patent Application No. 2.680.144.
Office Action dated Jun. 14. 2011 from Korean Patent Application No. 10-2009-7020746.
Official Notice dated Aug. 2, 2012 from Korean Application No. 10-2009-7020746.
Notification of the First Office Action dated Apr. 6, 2012 from Chinese Application No. 2008800143883.
Korean Office Action dated Aug. 2, 2012 for corresponding Korean Patent Application No. 10-2009-7020746 with English stunmary.
European Search Report dated Apr. 27, 2011 for corresponding European Patent Application No. 047606017.
English translation of First Office Action dated Apr. 6, 2012 for corresponding Chinese Patent Application No. 200880143883.
Office Action and English summary of Office Action previously dated Sep. 14, 2012.
Notification of the Second Office Action dated Nov. 30, 2012 from corresponding Chinese Application No. 2008800143883.
Supplementary European Search Report dated Dec. 17, 2012 from corresponding European Application No. 087264628.
Israeli Office Action for corresponding Israeli Patent Application No. 200734 with English summary dated Apr. 5, 2011.
Photocopy of box panels for QB. Silk Ease. Personal Fit Protection.
International Search Report from PCT Application No. PCT/US2008/02934. dated Jul. 14, 2008.
Written Opinion from PCT Application No. PCT/US2008/02934, dated Jul. 14, 2008.
Examination Report dated Aug. 25, 2011 from corresponding European Patent Application No. 04 760 601.7-1217.
"Retrieved from the internet on Mar. 3, 2010: http://www.inerriamwebstercom'dictionary/slit."
Canadian Examination Report dated Oct. 7, 2009, from corresponding Application No. 2,498,508.
Canadian Examination Report dated Dec. 18, 2008, from corresponding Application No. 2,498,508.
Canadian Examination Report dated Jan. 15, 2008, from corresponding Application No. 2,498,508.
Canadian Examnation Report dated May 3, 2008, from corresponding Application No. 2,498,508.
Notice of Reasons for Rejection dated Aug. 5, 2008, from corresponding Japanese Application No. 2004-536364.
Final Notice of Rejection dated May 12, 2009, from corresponding Japanese Application No. 2004-027399.
Official Action dated Apr. 26,2005, from corresponding Japanese Application No. 2004-27406.
Notice of Reasons for Rejection dated Oct. 4, 2011, from corresponding Japanese Application No. 2009/209408.
Official Action, from corresponding Mexican Application No. Pa/a/2005/002767.
U.S. Office Action dated Jun. 26, 2007, from corresponding U.S. Appl. No. 29/205,148.
U.S. Office Action dated Jun. 3, 2005, from corresponding U.S. Appl. No. 29/205,148.
U.S. Office Action dated May 16, 2005, from corresponding U.S. Appl. No. 29/201,235.
U.S. Office Action dated Oct. 1, 2007, from corresponding U.S. Appl. No. 29/201,242.
U.S. Office Action dated Aug. 25, 2005, from corresponding U.S. Appl. No. 29/201,242.
U.S. Office Action dated Jul. 2, 2007, from corresponding U.S. Appl. No. 29/201,242.
U.S. Office Action dated Jun. 9, 2009, from corresponding U.S. Appl. No. 10/242,474.
U.S. Office Action dated Dec. 16, 2008, from corresponding U.S. Appl. No. 10/242,474.
U.S. office Action dated May 5, 2008, from corresponding U.S. Appl. No. 10/242,474.
U.S. Office Action dated Dec. 20, 2006, from corresponding U.S. Appl. No. 10/242,474.
U.S. Office Action dated Jun. 16, 2006, from corresponding U.S. Appl. No. 10/242/474.
U.S. Office Action dated May 20, 2004, from corresponding U.S. Appl. No. 10/242,474.
U.S. Office Action dated Jan. 12, 2004, from corresponding U.S. Appl. No. 10/242,474.
U.S. Office Action dated Mar. 10, 2005, from corresponding U.S. Appl. No. 10/242,474.
U.S. Office Action dated Feb. 8, 2005, from corresponding U.S. Appl. No. 10/242,474.
U.S. Office Action dated Nov. 17, 2004, from corresponding U.S. Appl. No. 10/242,474.
U.S. Office Action dated Dec. 30, 2005, from corresponding U.S. Appl. No. 10/242,474.
2005 Gentle Glide Plastic Tampons.

ERGONOMIC TAMPON APPLICATOR

CROSS-REFERENCE TO RELATED APPLICATIONS

This is a continuation application of U.S. patent application Ser. No. 13/669,840 filed Nov. 6, 2012, which is a continuation application of U.S. patent application Ser. No. 12/798,990, filed Apr. 15, 2010, which is a continuation application of U.S. patent application Ser. No. 10/242,474, filed Sep. 12, 2002, claims the benefit of priority from U.S. Provisional patent application Ser. No. 60/499,443, filed on 2 Sep. 2003. Each of the above-noted applications is incorporated herein by reference.

BACKGROUND OF THE INVENTION

A. Field of Endeavor

The disclosure relates generally to an improved tampon or tampon applicator. More particularly, the present disclosure relates to a tampon applicator with a barrel that has a reverse taper section for improved ease of use and user comfort.

B. Description of the Prior Art

Commercial tampon applicators typically consist of a barrel and a plunger used to expel an absorbent pledget housed in the barrel. The barrel is typically sub-divided into three sections, namely a finger grip, an insertion tip, and a main body section, which is located between the finger grip and insertion tip sections.

The finger grip section is typically the same diameter as the main body section of the barrel, but some designs (e.g., Playtex® Gentle Glide®) have a reduced diameter grip for improve grippability. The main body section is typically linear, except on plastic molded barrels where there is a slight taper to improve release characteristics from the manufacturing mold. The insertion tip section on some types of barrels have "petals" which curve over and enclose the pledget (i.e., rounded tip) housed in the barrel, but readily flex outwardly as the pledget is expelled through the insertion tip.

SUMMARY OF THE INVENTION

The present disclosure provides a tampon applicator that is ergonomic.

The present disclosure also provides such an ergonomic tampon applicator with a plunger and a barrel.

The present disclosure further provides such an ergonomic tampon applicator barrel having a finger grip section, a reverse taper section, a main body section and an insertion tip section.

The present disclosure still further provides such an ergonomic tampon applicator barrel reverse taper section where the reverse taper is towards the finger grip section.

The present disclosure also provides such an ergonomic tampon applicator barrel finger grip section having a finger accepting region.

The present disclosure further provides such an ergonomic tampon applicator insertion tip section formed with a plurality of petals.

The present disclosure still further provides such an ergonomic tampon applicator main body section with a maximum diameter section that is sensually perceivable to a user to alert the user to the proper insertion depth of the applicator.

The present disclosure also provides such an ergonomic tampon applicator having a plunger with at least one flared end.

These and other objects and advantages of the present disclosure will be appreciated from an ergonomically improved tampon applicator having a plunger and a barrel, of the present disclosure. The barrel has four distinct sections, namely a finger grip section, a reverse taper section, a main body section, and an insertion tip section. The reverse taper section is tapered towards the fingergrip section, and the main body section is tapered in an opposite direction towards the insertion tip section. A maximum diameter is formed where the reverse taper section and main body section meet on the barrel. The maximum diameter provides a sensory indicator to the user to alert the user when the applicator has been inserted to the proper depth in the vagina.

DETAILED DESCRIPTION OF THE INVENTION

Figure 1:
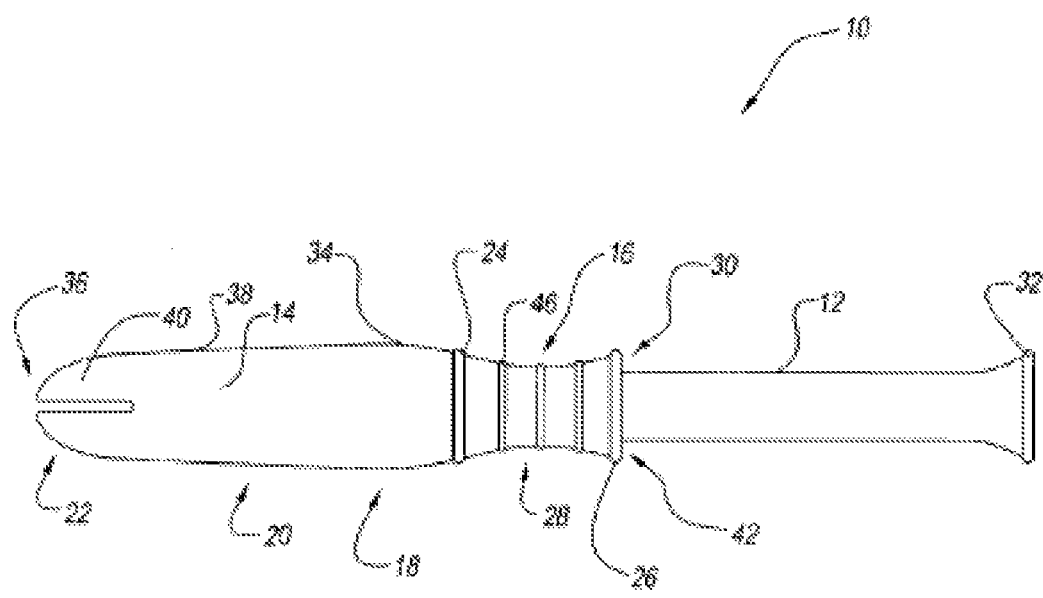
FIG. 1 is a plan view of a tampon applicator of the present disclosure.

Referring to FIG. 1, drawings and, in particular, FIG. 1, there is shown an ergonomically improved tampon applicator according to the present disclosure generally represented by reference numeral 10. The ergonomically improved applicator 10 is easier to use and more comfortable to insert and remove. Applicator 10 includes a plunger 12 and a barrel 14.

Barrel 14 may be divided into four sections, as opposed to three sections typically found in prior art tampon applicators. The four sections include a finger grip section 16, a reverse taper section 18, a main body section 20, and an insertion tip section 22.

Finger grip section 16 is bound by a forward edge ridge 24 and a rearward edge ridge 26. Forward edge ridge 24 provides a firm grip surface during insertion of applicator 10 into the vaginal vault. Rearward edge ridge 26 provides a firm grip surface during expulsion of the pledget (not shown) and during removal of applicator 10 from the body. Forward and rearward edge ridges 24, 26 are about 6 mm to about 22 mm in diameter. Preferably, the forward and rearward edges 24, 26 are about 11 mm to about 17 mm in diameter, with about 14 mm being the most preferred diameter.

A finger accepting region 28 is formed between forward edge ridge 24 and rearward edge ridge 26. To ensure an adequate area to accept a user's finger or fingers, forward edge ridge 24 and rearward edge ridge 26 are spaced about 13 mm to about 40 mm apart. More preferably, forward edge ridge 24 and rearward edge ridge 26 are spaced about 17 mm to about 21 mm apart, with about 19 mm being the most preferred spacing. Finger accepting region 28 may be concave, convex, flat, or any combinations thereof. Preferably, region 28 is concave, which conforms to the contour of a user's finger. The maximum diameter of region 28 is preferably slightly less than the diameter of edge ridges 24, 26.

Preferably, region 28 has a maximum to minimum diameter ratio of about 1.10 to about 1.75, with a more preferred ratio of about 1.25 to about 1.35.

Finger accepting region 28 may also include one or more gripping structures 46 to improve grippability of applicator 10. Suitable gripping structures 46 include, for example, one or more and preferably two or more, embossments, protuberances, slits, grooves, louvers, perforations, lances, abrasive medias, high wet coefficient of friction materials, pressure sensitive adhesives, or any combinations thereof. In addition, gripping structures 46 may be formed in any shape, including, for example, arc, circle, concave, cone, convex, diamond, line, oval, polygon, rectangle, rib, square, triangle, or any combinations thereof.

The maximum diameter 34 of applicator barrel 14 occurs at the forward end of reverse taper section 18. Reverse taper is meant to include a taper in the reverse direction, i.e. in a direction away from the insertion end of applicator 10, but not necessarily the same dimensional taper as main body section 20. The diameter of reverse taper section 18 tapers down toward forward edge ridge 24, where the diameter is equal to or slightly less than the diameter of forward edge ridge 24. This taper may be linear or curvilinear.

Maximum diameter 34 of barrel 14 exerts a slightly greater pressure than the smaller diameter portions of the barrel on the vaginal opening. This unique feature of barrel 14 provides a sensually perceivable way of signaling or indicating to a user that applicator 10 has been inserted to the correct depth in the vagina. Thus, the location of maximum diameter 34 along the length of barrel 14 is a critical aspect of the present disclosure. The location of maximum diameter 34 on barrel 14 is about 32 mm to about 54 mm in the axial direction of barrel 14 from forward end 36 of insertion tip 22. Preferably maximum diameter 34 is located about 40 mm to about 50 mm, and more preferably about 44 mm in the axial direction of barrel 14 from forward end 36 of insertion tip 22.

Main body section 20 is joined to reverse taper section 18 where maximum diameter 34 of barrel 14 is located. Main body section 20 tapers toward insertion tip section 22 in either a linear or curvilinear fashion so that its smallest diameter occurs where main body section 20 meets insertion tip section 22. The ratio of maximum diameter 34 to the diameter at the forward end 38 of main body section 20 is about 1.1 to about 1.5, and more preferably about 1.2 to about 1.3. This tapering of main body section 20 facilitates insertion comfort by gradually parting the vulva-vaginal channel over a longer length than that of only insertion tip section 22.

Insertion tip section 22 begins where there is a substantial change in the curvature of the forward portion of the barrel that is where the pledget-enclosing petals 40 are formed. In applicator designs where no petals are used, insertion tip 22 is the forward edge of the main body section 20 of barrel 14. The preferred insertion tip 22 is the petal type with a curvature that approximates an elliptical or hyperbolic curve. Preferably, insertion tip 22 has about 2 to about 12 petals, and more preferably about 3 to about 8 petals. The ratio of the maximum diameter of insertion tip section 22, which occurs at the plane where its rearward edge meets forward end 38 of main body section 20, to the total axial length of the insertion tip section along a horizontal axis of applicator 10, is about 0.9 to about 1.8, and more preferably about 1.1 to about 1.3.

The less severe curvature of insertion tip section 22 also facilitates insertion comfort by gradually parting the vulva-vaginal channel along its longer length.

It should be understood that while tampon applicator barrel 14 of the present disclosure is depicted as having four sections, namely a finger grip section, a reverse taper section, a main body section, and an insertion tip section, the tampon applicator barrel can include a reverse taper section and at least one additional section selected from a finger grip section, a main body section, an insertion tip section, or any combinations thereof.

The interior wall of barrel 14 that houses the pledget may have the same basic sidewall shape as its exterior wall. However, molding such a complicated interior wall requires a complex manufacturing process. Alternately, the interior wall can be practically straight walled (a slight taper may be required for tooling release) while the exterior wall has the sectional shapes discussed before, thus simplifying the molding process.

Figure 2:
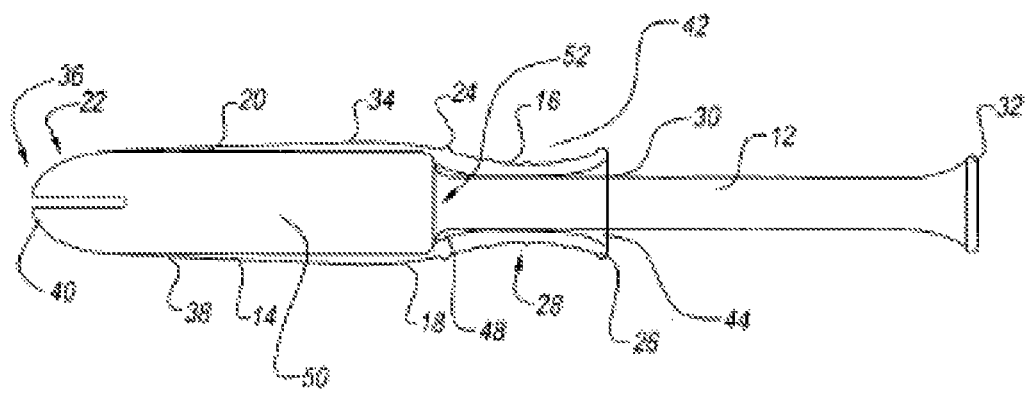
FIG. 2 is a cut away view of the tampon applicator of FIG. 1 depicting an absorbent pledget housed in the barrel.
Figure 3:
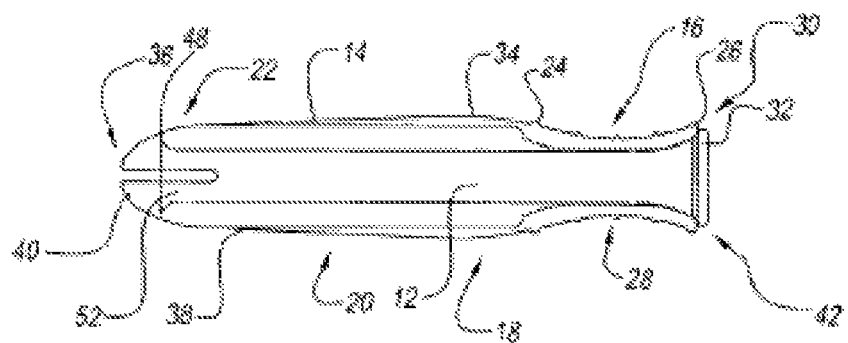
FIG. 3 is a cut away view of the tampon applicator of FIG. 2 after the pledget has been expelled from the barrel.

Referring to FIGS. 2 and 3, barrel 14 has a finger grip end 42. Plunger 12 telescopically fits into the finger grip end 42 of barrel 14. Plunger 12 has a diameter slightly smaller than the smallest diameter of finger receiving region 28 so that plunger 12 telescopically fits throughout the interior of barrel 14. Preferably, in one embodiment of the present disclosure, plunger 12 has a diameter about 4 mm to about 18 mm. More preferably, plunger 12 has a diameter about 5 mm to about 9 mm with the most preferred diameter being about 7 mm.

Plunger 12 has a first flare 32 at its distal end and a second flare or retaining structure 48 at its opposite barrel end 52. Finger grip section 16 has a plunger receiving end 30. Plunger receiving end 30 of finger grip section 16 has a chamfer 44 to receive first flare 32 of plunger 12 during pledget expulsion. This permits shortening the length of the section of plunger 12 that protrudes from barrel 14 since all of the protruded length is available for the telescopic action. This in turns results in a more ergonomic applicator. Such an ergonomic applicator is conducive to one handed use, since the distance between finger grip section 16 and first flare 32, where the fingertip is placed, is reduced by an amount equal to the length of first flare 32. Second flare or retaining feature 48 on barrel end 52 of plunger 12 prevents separation from barrel 14.

First flare 32 has a maximum diameter about 6 mm to about 22 mm. Preferably the maximum diameter is about 12 mm to about 16 mm, with about 13 mm being the most preferred maximum diameter, in order to provide a secure area for a user's fingertip during pledget expulsion. The rearward end of first flare 32 may be flat, concave, or convex. Preferably, it is concave to provide a secure area for the fingertip.

Second flare 48 has a maximum diameter about 5 mm to about 20 mm. Preferably the maximum diameter is about 11 mm to about 14 mm, with about 13 mm being the most preferred maximum diameter, in order to prevent separation from barrel 14.

Although it might be implied that the cross-sectional shape of plunger 12 and barrel 14 is circular, due to the use of the term 'diameter', it should be understood that the cross-sectional shape can be non-circular, such as oval or polygonal. Furthermore, the cross-sectional shape can vary along the length of both plunger 12 and barrel 14. For example, a circular plunger with a polygonal finger grip and an oval main body may be formed.

The pledget housed by applicator barrel 14 preferably has a tapered forward end that corresponds to that of insertion tip 22. The matching taper supports petals 40 during insertion of applicator 10 so that the petals cannot flex out of shape, thus enhancing comfort. Additionally, during expulsion from applicator 10, the pledget's tapered tip will gradually part the vaginal channel, further enhancing user comfort.

Suitable materials for forming plunger 12 and/or barrel 14 include, for example, biopolymer, cardboard, heat shrink plastic, paper slurry, plastic, plastic tubing, pulp slurry, pulp-molded paper, or any combinations thereof.

To reduce friction and/or increase strength, plunger 12 and/or barrel 14 may be coated with a coating material. Suitable coating materials include, for example, cellophane, cellulose, epoxy, lacquer, nitrocellulose, nylon, plastic, polyester, polylactide, polyolefin, polyvinyl alcohol, polyvinyl chloride, silicone, wax, or any combinations thereof.

The foregoing specification and drawings are merely illustrative of the present invention and are not intended to limit the invention to the disclosed embodiments. Variations and changes, which are obvious to one skilled in the art, are intended to be within the scope and nature of the present invention, which is defined in the appended claims.

The invention claimed is:

1. A tampon applicator, comprising:
    an insertion tip section having between three and eight petals;
    a main body section adjacent said insertion tip section, said main body section having a maximum diameter of said tampon applicator;
    a reverse taper section adjacent said main body section, wherein said reverse taper section tapers downwardly in a direction away from said insertion tip section; and
    a finger grip section having a forward end adjacent said reverse taper section, said finger grip section having a flared rearward end opposite said forward end defining an opening, wherein said finger grip section has at least one gripping structure, said finger grip section having a generally circular cross-sectional shape,
    wherein said finger grip section has a minimum diameter that is less than said maximum diameter of said main body section,
    wherein said flared rearward end has a rearward end diameter greater than said minimum diameter in said finger grip section,
    wherein said flared rearward end diameter is less than said maximum diameter of said main body section,
    wherein said at least one gripping structure has a grip structure diameter that is less than said flared rearward end diameter,
    wherein said tampon applicator has a straight central axis, and said insertion tip section, said main body section, said reverse taper section, and said finger grip section are all coaxially positioned around said central axis of said applicator,
    wherein said petals have a curved shape that taper towards said central axis.

2. The tampon applicator of claim 1, wherein said at least one gripping structure is a protuberance.

3. The tampon applicator of claim 1, wherein said at least one gripping structure is a rib.

4. The tampon applicator of claim 1, wherein said at least one gripping structure is a groove.

5. The tampon applicator of claim 1, wherein said at least one gripping structure has a coefficient of friction that is greater than a coefficient of friction of said main body section or said reverse taper section.

6. The tampon applicator of claim 1, wherein said finger grip section is concave.

7. The tampon applicator assembly according to claim 1, wherein said insertion tip section has said curved shape along said straight central axis that at least partially approximates at least one of an elliptical curved tapered shape and a hyperbolic curved tapered shape.

8. The tampon applicator according to claim 1, wherein said insertion tip section has a ratio of a maximum diameter of said insertion tip section to a length of said insertion tip section that is about 1.1 to about 1.3.

9. A tampon applicator assembly, comprising:
    a plastic applicator barrel having an internal cavity and a straight central axis, comprising:
        an insertion tip section having a generally curved tapered shape along said straight central axis, said insertion tip section having between three and eight petals;
        a main body section adjacent said insertion tip section, said main body section having a maximum diameter of said applicator barrel;
        a reverse taper section adjacent said main body section, wherein said reverse taper section tapers downwardly in a direction away from said insertion tip section; and
        a finger grip section having a forward end adjacent said reverse taper section, said finger grip section having a rearward end opposite said forward end said rearward end of said finger grip section defining an opening, said finger grip section having a generally concave shape between said forward end and said rearward end, said finger grip section including a plurality of gripping structures extending outward from an outer surface of said finger grip section between said forward end and said rearward end, said finger grip section having an external minimum grip diameter located between said forward end and said rearward end, said external minimum grip diameter is less than said maximum diameter of said applicator barrel in said main body section, said finger grip section having an internal minimum grip diameter; and
    a plunger that telescopically fits through said opening in said rearward end of said finger grip section, said plunger having a flared front end, a generally cylindrical middle region, and a flared rear end opposite said flared front end, said plunger having an external middle plunger diameter in said generally cylindrical middle region that is slightly smaller than said internal minimum grip diameter of said finger grip section,
    wherein said insertion tip section, said main body section, said reverse taper section and said finger grip section are all coaxially positioned around said straight central axis of said applicator barrel and are unitary such that said applicator barrel is a unitary plastic piece,
    wherein said applicator barrel includes a transition region in which a smaller wall thickness within said main body section as it transitions to a larger wall thickness in said reverse taper section and said finger grip section, said flared front end of said plunger engaging an internal wall within said transition region to retain said flared front end of said plunger in said applicator barrel.

10. The tampon applicator assembly of claim 9, wherein said external minimum grip diameter of said finger grip section is less than a grip structure diameter of said plurality of gripping structures.

11. The tampon applicator assembly according to claim 10, wherein said grip structure diameter of said plurality of gripping structures is less than said maximum diameter of said applicator barrel.

12. The tampon applicator assembly according to claim 11, wherein said plurality of gripping structures encircle said outer surface of said finger grip section.

13. The tampon applicator assembly of claim 9, wherein said generally concave shape of said finger grip section results in a ratio of a maximum external diameter of said finger grip section to said external minimum grip diameter of said finger grip section of about 1.1 to about 1.75.

14. The tampon applicator assembly according to claim 13, wherein said finger grip section has a ratio of said maximum external diameter of said finger grip section to said external minimum grip diameter of said finger grip section of about 1.25 to about 1.35.

15. The tampon applicator assembly according to claim 9, wherein said petals are discrete and separated from each other by a plurality of slits that form a break of material through a tubular wall of said applicator barrel.

16. The tampon applicator assembly according to claim 9, wherein said insertion tip section has said curved tapered shape along said central axis that at least partially approximates at least one of an elliptical curved tapered shape and a hyperbolic curved tapered shape.

17. The tampon applicator assembly according to claim 9, wherein said flared rear end of said plunger has a rear plunger diameter of about 6 mm to about 22 mm.

18. The tampon applicator assembly according to claim 17, wherein said flared rear end of said plunger has said rear plunger diameter of about 12 mm to about 16 mm.

19. The tampon applicator assembly according to claim 18, wherein said flared rear end of said plunger has said rear plunger diameter of about 12 mm.

20. The tampon applicator assembly according to claim 9, wherein said insertion tip section has a ratio of a maximum diameter of said insertion tip section to a length of said insertion tip section that is about 1.1 to about 1.3.

21. The tampon applicator assembly according to claim 9, wherein said insertion tip section has a tip end and a main body section end opposite said tip end, said main body section end adjacent said main body section, wherein said maximum diameter of said applicator barrel is between about 32 mm and about 54 mm from said tip end of said insertion tip section.

22. The tampon applicator assembly according to claim 9, wherein said maximum diameter of said applicator barrel is adjacent said reverse taper section.

23. The tampon applicator assembly according to claim 9, wherein said reverse taper section has a reverse taper diameter that is slightly less than a forward end grip diameter of said forward end of said finger grip section.

24. The tampon applicator assembly according to claim 9, wherein said generally concave shape of said finger grip section comprises one or more flat portions.

25. The tampon applicator assembly according to claim 9, wherein said plurality of gripping structures comprises a plurality of ribs sequentially positioned along a length of said finger grip section.

26. The tampon applicator assembly according to claim 25, wherein said plurality of ribs are sequentially positioned along the entirety of said length of said finger grip section.

27. The tampon applicator assembly according to claim 9, wherein said forward end of said finger grip section has a forward edge and said rewarded end of said finger grip section has a rearward edge.

28. The tampon applicator assembly according to claim 9, wherein said forward end of said finger grip section has a forward end grip diameter and said rearward end of said finger grip section has a rearward end grip diameter, wherein said forward end grip diameter and said rearward end grip diameter are about 11 mm to about 17 mm.

29. The tampon applicator assembly according to claim 9, wherein said forward end and said rearward end are spaced about 17 mm to about 21 mm apart.

30. The tampon applicator assembly according to claim 9, wherein a retaining structure comprises said flared front end of said plunger, wherein said flared front end of said plunger has a front plunger diameter of about 5 mm to about 20 mm.

31. The tampon applicator assembly according to claim 30, wherein said flared front end has said front plunger diameter of about 11 mm to about 14 mm.

32. The tampon applicator assembly according to claim 9, wherein said external middle plunger diameter of said middle region of said plunger is about 4 mm to about 18 mm.

33. The tampon applicator assembly according to claim 32 wherein said external middle plunger diameter of said middle region of said plunger is about 5 mm to about 9 mm.

34. A tampon assembly, comprising, comprising:
a plastic applicator barrel having an internal cavity and a straight central axis, said applicator barrel including:
an insertion tip section having between three and eight petals, said insertion tip section having a curved tapered shape along said central axis said insertion tip section having a front tip opposite a back end;
a main body section adjacent said back end of said insertion tip section, said main body section having a maximum diameter of said applicator barrel; said main body section having a main body section maximum wall thickness;
a reverse taper section adjacent said main body section, wherein said reverse taper section tapers downwardly in a direction away from said insertion tip section; and
a finger grip section adjacent said reverse taper section, said finger grip section having a forward edge adjacent said reverse taper section, said finger grip section having a rearward edge opposite said forward edge, said rearward edge defining an opening, said finger grip section having an external minimum grip diameter that is less than said maximum diameter of said applicator barrel, said finger grip section having an internal minimum grip diameter, said finger grip section having a circular cross-sectional shape and having a finger grip section maximum wall thickness that is greater than said main body section maximum wall thickness,
a plunger that fits through said opening in said rearward edge, said plunger having a flared front end, a generally cylindrical middle region, and a flared rear end, said flared rear end having a rear plunger diameter that is smaller than said rearward edge of said finger grip section, said flared front end having a front plunger diameter that is larger than said internal minimum grip diameter, said plunger having an external middle plunger diameter that is slightly smaller than said internal minimum grip diameter of said finger grip section, said plunger to be pushed forwardly toward said internal cavity along said straight central axis; and
a pledget within said internal cavity of said applicator barrel, said pledget including a tapered forward end;
wherein said insertion tip section, said main body section, said reverse taper section, and said finger grip section are all coaxially positioned around said central axis of said applicator barrel such that said applicator barrel is unitary.

35. The tampon assembly according to claim 34, wherein said insertion tip section has a ratio of a maximum diameter of said insertion tip section to a length of said insertion tip section that is about 1.1 to about 1.3.

36. The tampon assembly according to claim 34, wherein said insertion tip section has said curved tapered shaped along said straight central axis that at least partially approximates at least one of an elliptical curved tapered shape and a hyperbolic curved tapered shape.

37. The tampon assembly according to claim 34, wherein said pledget has said tapered forward end that corresponds to said insertion tip section.

38. The tampon assembly according to claim 34, wherein said maximum diameter of said applicator barrel is between about 32 mm and about 54 mm from said front tip of the insertion tip section.

39. The tampon assembly according to claim 34, wherein said maximum diameter of said applicator barrel is adjacent said reverse taper section.

40. The tampon assembly according to claim 34, wherein said reverse taper section is between about 50 mm and about 54 mm from said front tip of said insertion tip section.

41. The tampon assembly according to claim 34, wherein said reverse taper section has a reverse taper diameter that is less than said maximum diameter of said applicator barrel.

42. The tampon assembly according to claim 34, wherein said finger grip section is concave, flat, and combinations thereof.

43. The tampon assembly according to claim 34, wherein a distance between said forward edge of said finger grip section and said rearward edge of said finger grip section is between about 13 mm and about 40 mm.

44. The tampon assembly of claim 34, wherein said finger grip section further comprises at least one gripping structure.

45. The tampon assembly of claim 44, wherein said finger grip section has a minimum diameter less than a gripping structure diameter.

46. The tampon assembly according to claim 45, wherein said gripping structure diameter is less than said maximum diameter of said applicator barrel.

47. The tampon assembly according to claim 44, wherein said rearward edge of said finger grip section is flared and has a rearward grip diameter of said finger grip section that is greater than said external minimum grip diameter of said finger grip section.

48. The tampon assembly according to claim 47, wherein said rearward grip diameter of said finger grip section is less than said maximum diameter of said applicator barrel.

49. The tampon assembly according to claim 47, wherein said rearward grip diameter of said finger grip section is greater than a gripping structure diameter of said at least one gripping structure.

50. The tampon assembly according to claim 47, wherein said forward edge has a forward grip diameter and said rearward grip diameter are about 11 mm to about 17 mm.

51. The tampon assembly according to claim 44, wherein said at least one gripping structure encircles an outer surface of said finger grip section.

52. The tampon assembly according to claim 34, wherein a grip edge distance between said forward edge and said rearward edge is about 17 mm to about 21 mm.

53. The tampon assembly according to claim 34, wherein said finger grip section has a maximum to minimum diameter ratio of about 1.1 to about 1.75.

54. The tampon assembly according to claim 53, wherein said finger grip section has said maximum to minimum diameter ratio of about 1.25 to about 1.35.

55. The tampon assembly according to claim 34, wherein said external middle plunger diameter of said plunger is about 7 mm.

56. The tampon assembly according to claim 34, wherein said rear plunger diameter of said plunger is between about 12 mm and about 16 mm.

57. The tampon assembly according to claim 56, wherein said rear plunger diameter of said plunger is about 12 mm.

58. The tampon assembly according to claim 34, wherein said flared front end of said plunger engages an internal wall of said finger grip section such that said flared front end of said plunger is retained within said applicator barrel.

59. The tampon assembly according to claim 58, wherein said internal wall of said finger grip section is proximal said forward edge of said finger grip section.

60. The tampon assembly according to claim 34 or 59, wherein said forward edge corresponds to said finger grip section maximum wall thickness.

61. The tampon assembly according to claim 34, wherein said reverse taper section has a reverse taper section maximum wall thickness greater than said main body section maximum wall thickness.

62. The tampon assembly according to claim 61, wherein said reverse taper section maximum wall thickness is adjacent said finger grip section maximum wall thickness.

63. A tampon assembly, comprising:
a plastic applicator barrel having an internal cavity and a straight central axis, said applicator barrel including:
an insertion tip section having a generally curved tapered shape along said straight central axis, said insertion tip having between three and eight petals;
a main body section adjacent said insertion tip section, said main body section having a maximum diameter of said applicator barrel;
a reverse taper section adjacent to said main body section, said reverse taper section tapering downwardly in a direction away from said insertion tip section;
a finger grip section adjacent to said reverse taper section and being bound by a forward edge and a flared rearward edge, said reverse taper section tapering downwardly toward said forward edge, said finger grip section including a plurality of gripping structures extending away from a surface of said finger grip section between said forward edge and said rearward edge, each of said plurality of gripping structures extending around said finger grip section and having a maximum grip structure diameter that is less than a forward grip diameter of said forward edge and a rearward grip diameter of said flared rearward edge, said finger grip section including an opening leading into said internal cavity; and
wherein said insertion tip section, said main body section, said reverse taper section and said finger grip section are coaxially positioned around said straight central axis of said applicator barrel and are unitary such that said applicator barrel is a unitary plastic piece, said applicator barrel including a transition region in which a smaller wall thickness in said main body section transitions to a larger wall thicknesses in said reverse taper section and said finger grip section;
a pledget within said internal cavity of said applicator barrel, said pledget including a tapered forward end; and
a plunger that extends into said internal cavity of said applicator barrel through said opening in said finger grip section, said plunger having a flared front end, a generally cylindrical middle region, and a flared rear end, said flared rear end having a rear plunger diameter that is smaller than said rearward grip diameter of said rearward edge of said finger grip section, said flared front end having a front plunger diameter that is larger than an internal wall diameter within said transition region of said applicator barrel such that said plunger is retained within said applicator barrel.

64. The tampon assembly according to claim 63, wherein said insertion tip section has a ratio of a maximum diameter of said insertion tip to a length of said insertion tip that is about 1.1 to about 1.3.

65. The tampon assembly according to claim 63, wherein said insertion tip section has said curved tapered shape along said straight central axis that at least partially approximates at least one of an elliptical curved tapered shape and a hyperbolic curved tapered shape.

66. The tampon assembly according to claim 63, wherein said pledget has said tapered forward end that corresponds to said insertion tip section.

67. The tampon assembly according to claim 63, wherein said flared front end of said plunger is received within said petals of said insertion tip section as said plunger expels said pledget through said petals.

68. The tampon assembly according to claim 63, wherein said flared front end of said plunger extends beyond 50% of a length of said petals as said plunger expels said pledget through said petals.

69. The tampon assembly according to claim 63, wherein said insertion tip section has a thinnest wall thickness that is less than said smaller wall thickness of said main body section.

70. The tampon assembly according to claim 63, wherein an internal wall of said applicator barrel within said finger grip section includes a flared forward internal surface and a flared rearward internal surface.

71. The tampon assembly according to claim 70, wherein said internal wall of said applicator barrel within said finger grip section includes a generally cylindrical surface between said flared forward internal surface and said flared rearward internal surface.

72. The tampon assembly according to claim 70, wherein said flared rearward internal surface within said finger grip section is for engaging said flared rear end of said plunger as said plunger expels said pledget through said petals.

73. The tampon assembly according to claim 70, wherein said flared front end of said plunger engages said internal wall of said applicator barrel such that said flared front end of said plunger is retained within said applicator barrel.

74. The tampon assembly according to claim 70, wherein said flared forward internal surface corresponds to a finger grip section maximum wall thickness.

75. The tampon assembly according to claim 74, wherein said reverse taper section has a reverse taper section maximum wall thickness greater than said smaller wall thickness in said main body section.

76. The tampon assembly according to claim 75, wherein said reverse taper section maximum wall thickness is adjacent said finger grip section maximum wall thickness.

* * * * *